United States Patent
Lehmann et al.

(10) Patent No.: US 9,079,924 B2
(45) Date of Patent: Jul. 14, 2015

(54) METHOD FOR PRODUCING METAL COMPOUNDS

(75) Inventors: Frank Lehmann, Dudenhofen (DE); Udo Kittelmann, Rödermark (DE)

(73) Assignee: Bayer MaterialScience AG (DE)

( * ) Notice: Subject to any disclaimer, the term of this patent is extended or adjusted under 35 U.S.C. 154(b) by 321 days.

(21) Appl. No.: 13/504,753

(22) PCT Filed: Oct. 29, 2010

(86) PCT No.: PCT/EP2010/066502
§ 371 (c)(1),
(2), (4) Date: Oct. 9, 2012

(87) PCT Pub. No.: WO2011/051465
PCT Pub. Date: May 5, 2011

(65) Prior Publication Data
US 2013/0023685 A1   Jan. 24, 2013

(30) Foreign Application Priority Data
Oct. 30, 2009   (EP) .................... 09174652

(51) Int. Cl.
*C07F 7/22* (2006.01)
*C07F 7/00* (2006.01)
(52) U.S. Cl.
CPC ............. *C07F 7/003* (2013.01); *C07F 7/006* (2013.01)
(58) Field of Classification Search
CPC .......... C07F 7/006; C07F 7/28; C07F 7/2228; C07F 7/2232; C07F 7/003
USPC ............. 556/51, 54, 55, 81, 85, 105
See application file for complete search history.

(56) References Cited

U.S. PATENT DOCUMENTS

2011/0054140 A1   3/2011   Krause et al.

FOREIGN PATENT DOCUMENTS

| CN | 102015096 A | 4/2011 |
| DE | 242617 A1 | 2/1987 |
| DE | 102004011348 A1 | 9/2005 |
| DE | 102008021980 A1 | 11/2009 |
| EP | 1108752 | 6/2001 |
| GB | 899948 A | 6/1962 |
| WO | WO-2005/058996 A1 | 6/2005 |
| WO | WO 2009/132784 | 11/2009 |

OTHER PUBLICATIONS

International Search Report for PCT/EP2010/066502, mailing date Apr. 28, 2011.
Tzsahach, A. et al., "Zur Reaktivität von intermolekular basenstabilisierten Zinn(II)-Verbindungen mit Halogenen, Zinntetrachlorid und Chloroform", Z. An-Org. Allg. Chemie, vol. 512, pp. 177-180, (1984).
Shiryaev et al., "Synthesis $^1$H NMR Study of Some Organotin Derivatives of Diethanolamines", Russian Chemical Bulletin, vol. 43, No. 4 pp. 666-670 (Apr. 1994).
Sharma et al., "The First Butyltin (IV) homo- and Heterobimetallic Diethanolaminates", Phosphorus, Sulfur and Silicon, 181: pp. 2735-2744, (Nov. 2006).
Chinese Office Action for application No. 201080047777.3 dated Apr. 25, 2014.

*Primary Examiner* — Porfirio Nazario Gonzalez
(74) *Attorney, Agent, or Firm* — Drinker Biddle & Reath LLP

(57) ABSTRACT

The invention relates to processes for preparing metal(IV) compounds which are suitable especially as catalysts for preparation of polyesters, polyurethanes and polysiloxanes, and to the use of the metal compounds for preparation of polyesters, polyurethanes or polysiloxanes.

16 Claims, No Drawings

METHOD FOR PRODUCING METAL COMPOUNDS

The present invention relates to processes for preparing metal compounds which are suitable more particularly as catalysts for preparation of polyesters, polyurethanes or polysiloxanes, and to the use of the metal compounds for preparation of polyesters, polyurethanes or polysiloxanes.

Polyurethanes have long been known and are used in various sectors. Frequently, in the preparation of the polyurethanes, the actual polyurethane reaction has to be performed using catalysts since the reaction otherwise proceeds too slowly and may lead to polyurethane products with poor mechanical properties. In most cases, the reaction between the hydroxyl component and the NCO component has to be catalyzed.

The commonly used catalysts are generally divided into metallic and nonmetallic catalysts. Typical commonly used catalysts are, for example, amine catalysts, for instance 1,8-diazabicyclo[5.4.0]undec-7-ene (DBU), 1,4-diazabicyclo[2.2.2]octane (DABCO) or triethanolamine. The metallic catalysts are usually Lewis acid compounds such as dibutyltin or dioctyltin compounds, zinc octoate, lead octoate, tin octoate, titanium complexes and zirconium complexes, but also cadmium compounds, bismuth compounds (for example bismuth neodecanoate) and iron compounds.

One requirement of the catalyst is that it catalyzes only one of the various polyurethane reactions in a well-defined manner, for instance exclusively the reaction between OH and NCO groups. Side reactions, for example di- or trimerizations of isocyanate, allophanatizations, biuretizations, water reactions or urea formations should not be catalyzed at the same time. The requirement is to the effect that an optimal catalyst catalyzes exactly the reaction which is desired in the specific case; for example only the water reaction, so as to give rise to a defined foam profile or, as in the case of use of the potassium acetates, preferably the polyisocyanate reaction.

However, there are currently barely any catalysts which catalyze just one defined reaction. This would, however, be extremely desirable particularly with regard to the various possible reactions in polyurethane preparation. Of particular interest are therefore not just catalysts which catalyze only one reaction in a defined manner, but also catalysts which additionally become active in a controlled manner and catalyze specific reactions only under particular conditions. In such cases, reference is made to switchable catalysts. These switchable catalysts are in turn divided into thermally, photochemically and optically switchable catalysts. In general, reference is also made here to latent catalysts, and in the thermal case to thermolatent catalysts. These catalysts are inactive until the reaction mixture reaches a particular temperature. Above this temperature, they are then active. These latent catalysts enable long pot lives and fast demolding times.

The best known class of latent catalysts to date which may have been used consists of mercury compounds. The most prominent representative here is phenylmercuric neodecanoate (Thorcat 535 and Cucore 44). This catalyst has a latent reaction profile, the catalyst being initially virtually inactive and becoming abruptly active at a particular temperature (usually around 70° C.) only after gradual heating of the mixture, usually due to the exothermicity of the uncatalyzed reaction of NCO with OH groups. In the case of use of this catalyst, very long pot lives can be achieved with very short curing times. It is particularly advantageous when a very large amount of material has to be discharged (for example a large mold has to be filled) and, on completion of discharge, the reaction has to be ended rapidly and hence economically.

In the case of use of latent catalysts, it is particularly advantageous when the following conditions are additionally met:
(a) An increase in the amount of catalyst accelerates the reaction without any loss of catalyst latency.
(b) A reduction in the amount of catalyst slows the reaction without any loss of catalyst latency.
(c) A variation in the amount of catalyst, in the index of the mixing ratio, in the output rate and/or in the rigid segment content in the polyurethane does not impair the latency of the catalyst.
(d) In all aforementioned variations, the catalyst ensures virtually complete conversion of the reactants without leaving tacky sites.

A particular advantage of latent catalysts is considered to be that, in the finished polyurethane material, as a result of the decrease in their catalytic action with falling temperature, they only slightly accelerate the cleavage of urethane groups, for example at room temperature, compared to conventional catalysts. They therefore contribute to favorable sustained use properties of the polyurethanes.

Furthermore, in the case of use of catalysts, it should generally be ensured that the physical properties of the products are adversely affected to a minimum degree. This is also the reason why controlled catalysis of a particular reaction is so important. Specifically in the case of use of elastomers, especially of cast elastomers, the use of mercury catalysts is very widespread since they are widely usable, need not be combined with additional catalysts and catalyze the reaction between OH and NCO groups in a very controlled manner. The sole disadvantage, but a serious one, is the high toxicity of the mercury compounds, and so great efforts are being made to find alternatives thereto.

An overview of the prior art is given, for example, in WO 2005/058996 A1. There is a description here of how titanium catalysts and zirconium catalysts are employed. There is also mention of numerous possible combinations of various catalysts.

Systems which are at least less toxic than mercury catalysts, for example based on tin, zinc, bismuth, titanium or zirconium, but also amidine and amine catalysts, are known on the market but to date do not have the robustness and simplicity in the handling of the mercury compounds.

Particular combinations of catalysts have the effect that the gel reaction proceeds substantially separately from the curing reaction, since many of these catalysts act merely selectively. For example, bismuth(III) neodecanoate is combined with zinc neodecanoate and neodecanoic acid. Often, 1,8-diazabicyclo[5.4.0]undec-7-ene is additionally added. Even though this combination is one of the best known, it is unfortunately not as widely and universally usable as, for example, Thorcat 535 (from Thor Especialidades S.A.) and is additionally susceptible in the event of variations in formulation. The use of these catalysts is described, for example, in DE 10 2004 011 3481 A1.

The DABCO DC-2 product available on the market from Air Products Chemicals Europe B.V. is a catalyst mixture of 1,4-diazabicyclo[2.2.2]octane (DABCO) and dibutyltin diacetate. The disadvantage of this mixture is that the amine immediately has activating action. Alternative systems are, for example, Polycat SA-1/10 (from Air Products Chemicals Europe B.V.). This comprises acid-blocked DABCO. Even though this system is thermolatent, such systems are not used in the execution due to their poor catalytic action in the curing reaction. The elastomers produced in the presence of these systems remain tacky at the end of the reaction; reference is also made to the "starvation" of the reaction.

It is an object of the present invention to provide a process for preparing catalysts which can be used to obtain catalysts which enable preparation of polyisocyanate polyaddition products, polyesters or polysiloxanes with good mechanical properties. The catalysts prepared by the process according to the invention should additionally be free of toxic heavy metals, such as cadmium, mercury and lead, and themselves carry a lower intrinsic potential.

This object is achieved by the present invention by a process for preparing metal compounds of the general formula (I) or (II) or (III). The metal compounds of the general formula (I) are mononuclear metal compounds of metals of the (IV) oxidation state with at least one ligand containing at least one nitrogen and bonded via at least one oxygen or sulfur atom $$[(L^1)_{n1}(L^2)_{n2}(L^3)_{n3}(L^4)_{n4}(M)(IV)] \tag{I}$$

in which:
M=Sn, Ti, Zr or Hf,
n1, n2, n3, n4 are each 0 or 1 and $L^1$, $L^2$, $L^3$, $L^4$ are each mono-. di-, tri- or tetravalent ligands, where at least one ligand per M is defined as follows:

—X—Y where X=O, S, OC(O), OC(S), O(O)S(O), O(O)S(O)
Y=—$R^1$—N($R^2$)($R^3$) or —$R^1$—C($R^4$)=N$R^2$,
where $R^1$, $R^2$, $R^3$, $R^4$ are each independently saturated or unsaturated, cyclic or acyclic, branched or unbranched, substituted or unsubstituted hydrocarbyl radicals optionally interrupted by heteroatoms, or $R^2$, $R^3$, $R^4$ are each independently hydrogen, $R^1$—X, or $R^2$ and $R^3$ or $R^2$ and $R^1$ or $R^3$ and $R^1$ or $R^4$ and $R^1$ or $R^4$ and $R^2$ form a ring,
where the other ligands are each independently —X—Y as defined above or are defined as follows:
saturated or unsaturated, cyclic or acyclic, branched or unbranched, substituted or unsubstituted hydrocarbyl radicals optionally interrupted by heteroatoms, or halides, hydroxide, amide radicals, oxygen, sulfur, $R^2$ or $XR^2$, more preferably oxygen, sulfur, alkoxides, thiolates or carboxylates.

The metal compounds of the general formula (II) are dinuclear metal compounds of metals of the (IV) oxidation state with at least one ligand containing at least one nitrogen and bonded via at least one oxygen or sulfur atom per metal atom $$[(L^1)_{n1}(L^2)_{n2}(L^3)_{n3}(M)(IV)]_2O \tag{II}$$

in which:
M=Sn, Ti, Zr or Hf,
n1, n2, n3 are each 0 or 1 and $L^1$, $L^2$, $L^3$ are each mono-, di-, trivalent ligands, where at least one ligand per metal atom is defined as follows:

—X—Y where X=O, S, OC(O), OC(S), O(O)S(O), O(O)S(O)
Y=—$R^1$—N($R^2$)($R^3$) or —$R^1$—($R^4$)=N$R^2$,
where $R^1$, $R^2$, $R^3$, $R^4$ are each independently saturated or unsaturated, cyclic or acyclic, branched or unbranched, substituted or unsubstituted hydrocarbyl radicals optionally interrupted by heteroatoms, or $R^2$, $R^3$, $R^4$ are each independently hydrogen, $R^1$—X, or $R^2$ and $R^3$ or $R^2$ and $R^1$ or $R^3$ and $R^1$ or $R^4$ and $R^1$ or $R^4$ and $R^2$ form a ring, where the other ligands are each independently —X—Y as defined above or are defined as follows:
saturated or unsaturated, cyclic or acyclic, branched or unbranched, substituted or unsubstituted hydrocarbyl radicals optionally interrupted by heteroatoms, or halides, hydroxide, amide radicals, oxygen, sulfur, $R^2$ or $XR^2$, more preferably oxygen, sulfur, alkoxides, thiolates or carboxylates.

The metal compounds of the general formula (III) are di- or polynuclear tetravalent metal compounds of metals of the (IV) oxidation state with at least one ligand containing at least one nitrogen and bonded via at least one oxygen or sulfur atom per metal atom $$[(L^1)_{n1}(L^2)_{n2}(M)(IV)]_n \tag{III}$$

where
M=Sn, Ti, Zr or Hf,
n1, n2 are each 0 or 1, n is greater than or equal to 2 and $L^1$, $L^2$ are each mono-, divalent ligands, where at least one ligand per M atom is defined as follows:

—X—Y where X=O, S, OC(O), OC(S), O(O)S(O), O(O)S(O)
Y=—$R^1$—N($R^2$)($R^3$) or —$R^1$—C($R^4$)=N$R^2$,
where $R^1$, $R^2$, $R^3$, $R^4$ are each independently saturated or unsaturated, cyclic or acyclic, branched or unbranched, substituted or unsubstituted hydrocarbyl radicals optionally interrupted by heteroatoms, or $R^2$, $R^3$, $R^4$ are each independently hydrogen, $R^1$—X, or $R^2$ and $R^3$ or $R^2$ and $R^1$ or $R^3$ and $R^1$ or $R^4$ and $R^1$ or $R^4$ and $R^2$ form a ring,
where the other ligands are each independently —X—Y as defined above or are defined as follows:
saturated or unsaturated, cyclic or acyclic, branched or unbranched, substituted or unsubstituted hydrocarbyl radicals optionally interrupted by heteroatoms, or halides, hydroxide, amide radicals, oxygen, sulfur, $R^2$ or $XR^2$, more preferably oxygen, sulfur, alkoxides, thiolates or carboxylates.

"Hydrocarbyl radicals" or "alkyl" in the context of the present invention generally mean preferably a saturated aliphatic hydrocarbyl group which may be straight-chain or branched and may have from 1 to 30 carbon atoms in the chain. Preferred alkyl groups may be straight-chain or branched and have from 1 up to 12 carbon atoms in the chain. "Branched" means that a lower alkyl group having 1 to 7 carbon atoms, such as methyl, ethyl or propyl, is attached to a linear alkyl chain. Hydrocarbyl radical and alkyl are, for example, methyl, ethyl, 1-propyl, 2-propyl, 1-butyl, 2-butyl, 2-methyl-1-propyl (isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 2-ethylhexyl, 1-nonyl, 1-decyl, 1-undecyl, 1-dodecyl, 1-tetradecyl, 1-hexadecyl and 1-octadecyl.

Analogous preferences apply, where chemically possible, to hydrocarbyl radicals defined as alkylene, alkenyl, alkenylene, alkynyl, alkynylene, cycloalkyl, cycloalkylene, cycloalkenyl or cycloalkenylene.

"Substituted alkyl" means preferably that the alkyl group is substituted by one or more substituents selected from alkyl, optionally substituted aryl, optionally substituted aralkyl, alkoxy, nitro, carboalkoxy, cyano, halo, alkylmercaptyl, trihaloalkyl or carboxyalkyl. The same applies to the other possible hydrocarbyl radicals.

"Cycloalkyl" means an aliphatic ring which has from 3 to about 10 carbon atoms in the ring. Preferred cycloalkyl groups have from 4 to about 7 carbon atoms in the ring.

"Alkoxy" means an alkyl-O— group in which "alkyl" is as defined above. Lower alkoxy groups are preferred. Illustrative groups include methoxy, ethoxy, n-propoxy, i-propoxy, s-butoxy, t-butoxy and n-butoxy.

"Lower alkyl" means an alkyl group which has 1 to about 7 carbon atoms.

"Alkoxyalkyl" means an alkyl group as described above, which is substituted by an alkoxy group as described above.

"Halogen" (or "halo") means chlorine (chloro) fluorine (fluoro), bromine (bromo) or iodine (iodo).

The process according to the invention for preparing the metal compounds of the general formula (I) or (II) or (III), as defined above, comprises the steps of (a) providing a compound of the formula $ML_4$ where L is independently R, OR or Hal, where R=$C_1$ to $C_8$-alkyl, Hal=Cl, Br or I and M=Sn, Ti, Zr or Hf, and (b) reacting the compounds provided in process step (a) with at least one compound of the formula H—X—Y and/or M'—X—Y,
where X and Y are each as defined above and $M^1$=Li, Na, K, Ca, Mg or $NH_4^+$, preferably in at least one solvent.

The process according to the invention is characterized in that the reaction in process step (b) is performed in the presence of one or more compounds selected from $NH_3$, primary, secondary and tertiary amines, $M^2OH$ and $M^2O$—$R^5$, where $R^5$ is a hydrocarbyl radical having 1 to 6 carbon atoms and $M^2$ is $Li^+$, $Na^{30}$, $Ca^{2+}$ or $Mg^{2+}$.

In a preferred embodiment of the invention, the reaction in process step (b) is performed in the presence of one or more compounds selected from $NH_3$, 1,4-diazabicyclo[2.2.2]octane-1,8-diazabicyclo[5.4.0]non-5-ene, triethylamine, triethyldiamine, N-methylimidazole, N,N-dimethylethanolamine, N-methylmorpholine, N-ethylmorpholine, 2,2-dimorpholinodiethyl ether, bis(2-dimethylaminoethyl)ether, N-benzyldimethylamine, N,N'-dimethylcyclohexylamine, $M^2OH$ and $M^2O$—$R^5$ where $R^5$ is a hydrocarbyl radical having 1 to 4 carbon atoms and $M^2$ is $Li^+$, $Na^+$, $K^+$, $Ca^{2+}$ or $Mg^{2+}$.

In a preferred embodiment of the invention, the compound in whose presence the reaction in process step (b) is undertaken is selected from the group of $NH_3$, $NaOC_2H_5$, $KOC_2H_5$, $NaOCH_3$ (sodium methoxide) and $KOCH_3$. In a particularly preferred embodiment of the invention, the compound is $NaOCH_3$ or $KOCH_3$.

The compound of the formula $ML_4$ which is provided in process step (a) is more preferably $SnCl_4$.

The amount of the above-defined compounds in whose presence process step (b) is performed can vary over wide ranges and is generally 0.7 to 1.3:1, preferably 0.9 to 1.1:1, based on the molar ratio of the compound to the metal. Particular preference is given to using the above-defined compound in whose presence process step (b) is performed in an equimolar amount relative to the metal.

The process according to the invention permits preparation of the metal compounds of the general formula (I) or (II) or (III) in high purity, for example with low reactant contaminations, such as chloride contents, and in high yield. Especially in the case of preparation of metal compounds of the general formula (I), it is possible to prepare the target structure with a low proportion of dimeric or oligomeric by-products. The yields achieved, for example in the case of preparation of tin metal compounds, are in the region of >97%, based on the tin used. The metal compounds prepared by the process according to the invention are colorless to yellowish, transparent and storage-stable over several months.

According to the invention, it is advantageous when the process according to the invention, in the case of preparation of metal compounds of the general formula (I), is performed with anhydrous raw materials whose water content is <0.1% by weight. Additionally preferably, the reaction in process step (b) is performed under an inert gas atmosphere, preferably under a nitrogen atmosphere, more preferably under a dry nitrogen atmosphere.

The metal of the metal compounds of the general formula (I) or (II) or (III) is generally selected from the group of tin, titanium, zirconium and hafnium, all of the aforementioned metals being present in the +IV oxidation state. In a preferred embodiment of the invention, the metal is tin or titanium; in a particularly preferred embodiment of the invention, the metal is tin.

Ligands (L) other than the specific ligand are generally ligands known from metal chemistry. These ligands may independently be bonded to the corresponding metal partly or exclusively via carbon (organic metal compounds/metal organyls). The hydrocarbyl radicals bonded directly to the metal are preferably saturated alkyl radicals having 1 to 30 carbon atoms, more preferably having 1 to 8 carbon atoms. The ligands may independently also be bonded to the metal exclusively via non-carbon atoms (inorganic metal compounds). The inorganic metal compounds—i.e. metal compounds without metal-carbon bonds—are preferred due to their low toxicity.

The ligands other than the specific ligand are preferably oxygen bridges, hydroxide, alkoxides, sulfonates, phosphonates, carboxylates, thiolates (in each case preferably having 1 to 30 carbon atoms, more preferably having 1 to 12 carbon atoms) and halides (preferably chloride and bromide), the ligands more preferably being bonded to the metal via oxygen, for example as an oxygen bridge, as hydroxide or in the form of an alkoxy group (alkoxide) or as a carboxylate.

Preferred alkoxide ligands are MeO—, EtO—, PrO—, iPrO—, BuO—, tBuO—, iBuO—, PhO— and:

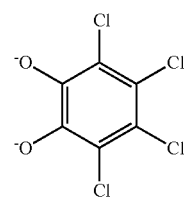

Me=methyl-, Et=ethyl, Pr=propyl, iPr=isopropyl, Bu=n-butyl, tBu=tert-butyl, iBu=isobutyl, Ph=phenyl radical.

Preferred carboxylate ligands are formate, acetate, propanoate, butanoate, pentanoate, hexanoate, neodecanoate, ethylhexanoate, laurate, lactate, benzoate, and one or more different natural fatty acids, particular preference being given to ethylhexanoate, laurate, neodecanoate and benzoate.

The metal compounds of the above-defined general formulae, especially the tin compounds thereof, tend—as is common knowledge—to oligomerize, and so polynuclear metal compounds, especially polynuclear tin compounds or mixtures of mono- and polynuclear metal compounds, are frequently present. In the polynuclear metal compounds, the metal atoms are preferably joined to one another via oxygen atoms.

Typical oligomeric complexes, for example polynuclear tin compounds, form, for example, as a result of condensation of the tin atoms via oxygen or sulfur, for example $[OSn(O-R^1-N(R^2)-R^1-O)]_n$ where n>1. In the case of low oligomerization rates, cyclic oligomers, and in the case of higher oligomerization rates linear oligomers with OH end groups, are frequently encountered.

In the case of specific —X—Y ligands, X is preferably oxygen, sulfur or —OC(O)—.

Preferably, the —X—Y ligand is a ligand in which X is sulfur or oxygen and Y is —CH$_2$CH$_2$N(R)CH$_2$CH$_2$S or —CH$_2$CH$_2$N(R)CH$_2$CH$_2$O, where R is preferably Me, Et, Bu, tBu, Pr, iPr or Ph.

Likewise preferably, the —X—Y ligand is a ligand in which X is —O—C(O)— and Y—CH$_2$—N(R)CH$_2$C(O), where R is preferably Me, Et, Bu, tBu, Pr, iPr, Ph.

Another preferred specific ligand is:

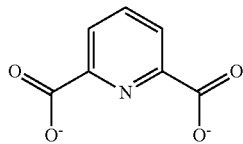 [SMILES: O=C([O-])c1cccc(C(=O)[O-])n1]

Further preferred specific —X—Y ligands are:
Me$_2$NCH$_2$CH$_2$O—, Et$_2$NCH$_2$CH$_2$O—, Me$_2$NCH$_2$CH(Me)O—, Bu$_2$NCH$_2$CH$_2$O—, Me$_2$NCH$_2$CH$_2$O—, PhN(H)CH$_2$CH$_2$O—, PhN(Et)CH$_2$CH$_2$O—, HN[CH$_2$CH$_2$O—]$_2$, —OCH$_2$CH$_2$N(H)CH$_2$CH$_2$CH$_2$O—, HN[CH$_2$CH(Me)O—]$_2$, MeN[CH$_2$CH$_2$O—]$_2$, BuN[CH$_2$CH$_2$O—]$_2$, PhN[CH$_2$CH$_2$O—]$_2$, MeN[CH$_2$, CH(Me)O—]$_2$, BuN[CH$_2$CH(Me)O—]$_2$, PhN[CH$_2$CH(Me)O—]$_2$, N[CH$_2$CH$_2$O—]$_3$, N[CH$_2$CH(Me)O—]$_3$,

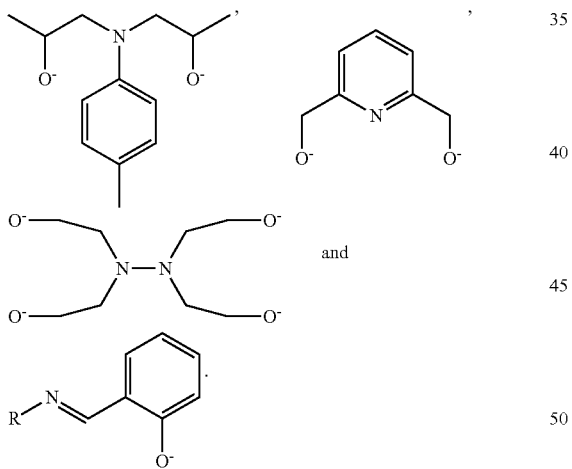

and

In a preferred embodiment, the invention relates to a process for preparing a tin compound is of the formula (R'O)(R"O)Sn(X—R$^1$—N—R$^1$—X, prepared with X=O, S, OC(O), preferably O and OC(O), more preferably O, where the R' and R" radicals may be the same or different. The R$^1$ radicals may be different or the same and are each as defined above. The R$^2$ radical is as defined above. In a particularly preferred embodiment, the R' and R" radicals are identical, as are the two R$^1$ radicals. The R' and R", and also R$^2$ radicals are preferably alkyl radicals. The R$^1$ radical is preferably —(CH$_2$)$_n$— where n is preferably 2. R$^2$ is preferably, and R' and also R", methyl, butyl, propyl or isopropyl. The R'O and R"O radicals may also be replaced by oxygen atoms, in which case a dinuclear tin compound bonded via two oxygen bridges is obtained. This is a special case of the oligomeric tin(IV) compounds described [Sn(O—R$^1$—N(R$^2$)—R$^1$—O]$_n$ where n>1.

The following formulae Ia to Ij illustrate some examples of the metal compounds prepared in accordance with the invention:

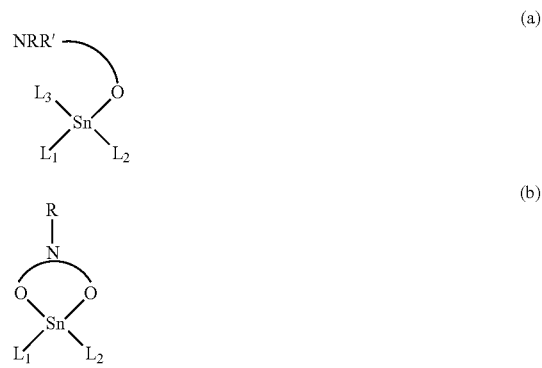

(a)

(b)

(c)

(d)

(e)

(f)

(g)

-continued (h)
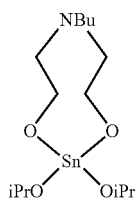

(i)
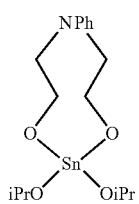

(j)
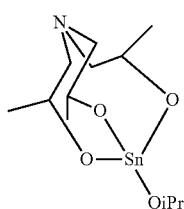

The formulae Ik to In show oligoinerized (for example dimerized) compounds.

(k)
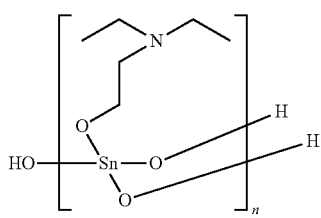

(l)
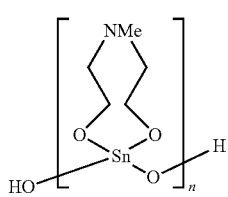

(m)
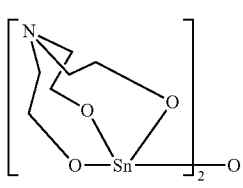

(n)
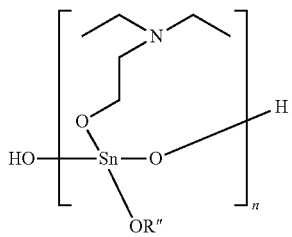

In a preferred embodiment of the invention, the process according to the invention is used to prepare a catalyst of the formula $[(L^1)_{n1}(Cl)_n(Sn)(IV)]$, more preferably N-methyldiethanolaminotin dichloride or N-ethyldiethanolaminotin dichloride.

The stoichiometric ratio of metal to ligand is generally in the range from 1:0.8 to 1:1.2; in a preferred embodiment, the at least one compound of the formula HXY and/or $M^1XY$ which is converted in process step (b) is converted to the metal used in a stoichiometric amount.

In general, the reaction of the metal halide with the at least one compound of the formula —X—HXY and/or $M^1XY$, as defined above, is performed in at least one solvent. The solvent in which the reaction is performed in process step (b) is generally selected from the group of the polyethylene glycols, polypropylene glycols, glycerol, glyceryl carbonate, $C_1$-$C_5$-alcohols such as methanol, ethanol, n-propanol, i-propanol, n-butanol, isobutanol, sec-butanol, tert-butanol, 1,2-propanediol, 1,3-propanediol, ethylene glycol, diethylene 1,2-propylene glycol, 1,3-propylene glycol, 1,2-butanediol, 1,3-butanediol, 2,3-butanediol, 1,4-butanediol, neopentyl glycol, diethylene glycol monomethyl ether and diethylene glycol. The solvent may also be a mixture of two, three, tour or five of the aforementioned solvents. In a preferred embodiment of the invention, the reaction in process step (b) is performed in a solvent of the above-defined formula H—X—Y.

In general, the reaction in process step (b) is performed at a temperature in the range from 40 to 120° C., preferably at a temperature in the range from 60 to 80° C. The reaction is performed over a period of about 0.5 h to about 3 h. The metal compounds prepared in accordance with the invention can be used for production of flexible and rigid polyurethane foams, coatings, adhesives and sealants, semirigid foams, integral foams, spray and cast elastomers, thermoplastic polyurethanes, resins and binders. In addition, the metal compounds prepared in accordance with the invention can be used for preparation of polyisocyanates, polyaddition products, for performance of esterifications and transesterifications, for performance of polyaddition and polycondensation reactions, and for preparation of polyesters and alkyd resins, and also for curing of epoxy and silicone compositions.

The following examples illustrate the invention:

EXAMPLES

Example 1

Preparation of N-methyldiethanolaminotin oxide

Approx. 360 g of ammonia were introduced into a solution of 1000 g of tin tetrachloride in 6650 g of isopropanol. Subsequently, the ammonium chloride was filtered off. An approx. 16% solution of tin tetraisopropoxide in isopropanol was obtained. At a temperature of 70° C., 352 g of N-methyldiethanolamine were added to 6208 g of this solution and the mixture was kept at 70° C. for 1½ h. An approx. 20% solution of the target compound in isopropanol was obtained. Reprecipitation in 1,4-butanediol with distillative removal of isopropanol under reduced pressure afforded the 20% partial solution in 1,4-butanediol.

Elemental analysis: Sn=7.0% N=0.8 % Cl<01%

119Sn NMR: δ −454 ppm

Example 2

Preparation of bis(N-methyldiethanolamino)tin 450 g of methyldiethanolamine were metered into a solution of 500 g of tin tetrachloride in 3110 g of polyethylene glycol. Then approx. 125 g of ammonia were introduced. Subsequently, ammonium chloride is filtered off. An approx. 16% solution of bis(N-methyldiethanolamino)tin in polyethylene glycol was obtained.

Elemental analysis: Sn=5.8% N=1.3%
119Sn NMR: δ −450 ppm

Example 3

Preparation of N-methyldiethanolaminotin dichloride 165 g of tin tetrachloride were metered into 1335 g of solution according to process example 2 and then the mixture was heated to 100° C. and kept at this temperature for 2 hours. 1500 g of an approx. 26% solution of N-methyldiethanolaminotin dichloride in polyethylene glycol were obtained, which were diluted to approx. 20% by addition of 400 g of polyethylene glycol. As well as the dichloride, the solution also contained significant proportions of mono- or trichloride.

Elemental analysis: Sn=7.6% N=0.8% Cl=4.5%
119Sn NMR: δ −494 ppm (impurities −490 and −496 ppm)

Example 4

Preparation of N-methyldiethanolaminotin dichloride 93.8 g of N-methyldiethanolamine tin were metered into a solution of 205 g of tin tetrachloride in 980 g of polyethylene glycol and then the mixture was heated to 80° C. Then 283.4 g of a 30% methanolic solution of sodium methoxide were metered in, in the course of which the temperature was kept at 80° C. Subsequently, the mixture was kept at this temperature for another hour. Then the sodium chloride precipitate was filtered off and the methanol was distilled off under reduced pressure. 1220 g of an approx. 20% solution of N-methyldiethanolaminotin dichloride in polyethylene glycol were obtained.

Elemental analysis: Sn=7.4% N=0.9% Cl=4.4%
119Sn NMR: δ −494 ppm

Example 5

Preparation of diethyleneglycolatotin dichloride 27.8 g of diethylene glycol were metered into a solution of 68.3 g of tin tetrachloride in 635 g of isopropanol and then the mixture was heated to 60° C. Then 94.5 g of a 30% methanolic solution of sodium methoxide were metered in, in the course of which the temperature was kept at 60° C. Subsequently, the mixture was kept at this temperature for another hour. 795 g of an approx. 10% solution of diethyleneglycolatotin dichloride in an isopropanol/methanol mixture were obtained.

Elemental analysis: Sn=4.1% N=2.4%

Example 6

Preparation of N-methyldiethanolaminotin chloride dimer 93.8 g of N-methyldiethanolaminotin chloride were metered into a solution of 205 g of tin tetrachloride in 980 g of polyethylene glycol. Then 283.4 g of a 30% methanolic solution of sodium methoxide were metered in, in the course of which the temperature rose to approx. 50° C. Then the mixture was heated to 60° C. Thereafter, 70.9 g of a 10% methanolic solution of water were metered in and the mixture was subsequently kept at 60° C. for another hour. Then the sodium chloride precipitate was filtered off and the methanol was distilled off under reduced pressure. 1200 g of an approx. 20% solution of N-methyldiethanolaminotin chloride dimer in polyethylene glycol were obtained.

Elemental analysis: Sn=7.6% N=0.9% Cl=2.3%

Example 7

Preparation of N-methyldiethanolaminotin chloride oligomer 93.8 g of N-methyldiethanolamine were metered into a solution of 205 g of tin tetrachloride in 980 g of polyethylene glycol. Then 283.4 g of a 30% methanolic solution of sodium methoxide were metered in, in the course of which the temperature rose to approx. 50° C. Then the mixture was heated to 60° C. Thereafter, 83.0 g of a 10% methanolic solution of water were metered in and the mixture was subsequently kept at 60° C. for another hour. Then the sodium chloride precipitate was filtered off and the methanol was distilled off under reduced pressure. 1200 g of an approx. 20% solution of N-methyldiethanolaminotin chloride oligomer in polyethylene glycol were obtained.

Elemental analysis: Sn=7.7% N=0.9% Cl=2.2%

Examle 8

Preparation of N-butyldiethanolaminotin dichloride 63.4 g of N-butyldiethanolamine were metered into a solution of 102.5 g of tin tetrachloride in 500 g of polyethylene glycol. Subsequently, 141.7 g of a 30% methanolic solution of sodium methoxide were metered in, in the course of which the temperature was limited to 60° C. Subsequently, the mixture was kept at 60° C. for another hour. Then the sodium chloride precipitate was removed and the methanol was distilled off under reduced pressure. 635 g of approx. 20% solution of N-butyldiethanolaminotin dichloride in polyethylene glycol were obtained.

Elemental analysis: Sn=7.0% Cl=4.5 AN=48
(AN means the amine number, i.e. the amount of KOH in mg which corresponds to the amine content of 1 g of substance. The amine number can be determined to DIN 53176.)
119Sn NMR: δ −496 ppm Example 9

Preparation of N-p-toluyldiethylanolaminotin chloride 76.8 g of N-toluodiethanolamine were metered into a solution of 102.5 g of tin tetrachloride in 500 g of polyethylene glycol. Subsequently, 141.7 g of a 30% methanolic solution of sodium methoxide were metered in, in the course of which the temperature was limited to 60° C. Subsequently, the temperature was kept at 60° C. for another hour. Then the sodium chloride precipitate was removed and the methanol was distilled off under reduced pressure. 650 g of an approx. 20% solution of N-toluodiethanolaminotin dichloride in polyethylene glycol were obtained.

Elemental analysis: Sn=6.9% Cl=4.6 AN=47

Use Example 1

667.4 g of soybean oil, 148.8 g of pentaerythritol and 0.5 g of catalyst according to process example 4 were heated to 240° C. in a 1 l four-neck flask with stirrer, temperature control, nitrogen supply and condenser. After one hour, the transesterification was substantially complete and the mixture was cooled to 160° C. Then 247 g of phthalic anhydride, 2.4 g of maleic anhydride and a sufficient amount of xylene as an entraining agent were added and azeotropic esterification was effected at 230° C. After three hours of reaction time, an acid number of 5 and a viscosity (50% in xylene) of 150 mPas was attained.

Use Example 2

624 g of neopentyl glycol, 102 g of adipic acid, 680 g of isophthalic acid and 0.8 g of catalyst solution according to process example 4 were heated to 230° C. in a 1 l four-neck flask with stirrer, temperature control, nitrogen supply and column such that the temperature at the top of the column did not exceed 102° C. After six hours of reaction time, the acid number had gone below 5.

Use Example 3

100 g of a silicone resin (100%, OH content 3.5-7.0%, melting point approx. 65° C.) were mixed vigorously with 2.5 g of the inventive catalyst (solvent-free). The mixture was melted into an aluminum pan and heated homogeneously at a heating rate of 1 K/min. The gelation temperature was determined to be 152° C. through tearing of threads. The resulting test specimen was fully crosslinked and had good demoldability.

Use Example 4

100 g of a silicone resin (100%, OH content 3.5-7.0%, melting point approx. 65° C.) was melted without catalyst in an aluminum pan and heated homogeneously to 200° C. at a heating rate of 1 K/min and heated at this temperature for 10 minutes. No crosslinking was found. The resulting test specimen was not demoldable without destruction.

The invention claimed is:

1. A process for preparing metal compounds of the general formula (I), (II) or (III) with at least one ligand containing at least one nitrogen and bonded via at least one oxygen or sulfur atom $$[(L_1)_{n1}(L^2)_{n2}(L^3)_{n3}(L^4)_{n4}(M)(IV)] \qquad (I)$$

$$[(L^1)_{n1}(L^2)_{n2}(L^3)_{n3}(M)(IV)]_2 O \qquad (II)$$

$$[(L^1)_{n1}(L^2)_{n2}(M)(IV)]_n \qquad (III)$$

M is Sn, Ti, Zr or Hf, n1, n2, n3, n4 are each 0 or 1 and n is greater than or equal to 2, $L^1$, $L^2$, $L_3$, $L_{b\,4}$ each mono-, di-, tri- or tetravalent ligands, where at least one ligand per M is defined as follows:

—X—Y in which

X is O, S, OC(O), OC(S), O(O)S(O),

Y is —R$^1$—N(R$^2$)(R$^3$) or —R$^1$—C(R$^4$)=NR$^2$, in which R$^1$, R$^2$, R$^3$ and R$^4$ are each independently saturated or unsaturated, cyclic or acyclic, branched or unbranched, substituted or unsubstituted hydrocarbyl radicals optionally interrupted by heteroatoms, or R$^2$, R$^3$, R$^4$ are each independently hydrogen, R$^1$—X, or R$^3$ or R$^2$ and R$^1$ or R$^3$ and R$^1$ or R$^4$ and R$^1$ or R$^4$ and R$^2$ form a ring, where the remaining ligands are each independently —X—Y as defined above or are defined as follows:

saturated or unsaturated, cyclic or acyclic, branched or unbranched, substituted or unsubstituted hydrocarbyl radicals optionally interrupted by heteroatoms, or halides, hydroxides, amide radicals, oxygen, sulfur, R$^2$ or XR$^2$, comprising the steps of (a) providing a compound of the formula ML$_4$ where L is independently R, OR or Hal, where: R=C$_1$ to C$_8$-alkyl, Hal=Cl, Br or I and M=Sn, Ti, Zr or Hf, and (b) reacting the compound provided in process step (a) with at least one compound of the formula H—X—Y and/or M$^1$-X—Y, where X and Y are each as defined above and, M$^1$=Li, Na, K, Ca, Mg, or NH$_4^+$ characterized in that the reaction in process step (b) is performed in the presence of one or more compounds selected from NH$_3$, primary, secondary and tertiary amines, M$^2$OH and M$^2$O—R$^5$, where R$^5$ is a hydrocarbyl radical having 1 to 6 carbon atoms and M$^2$ is Li$^+$, Na$^+$, Ca$^{2+}$ or Mg$^{2+}$.

2. The process as claimed in claim 1, characterized in that the reaction in process step (b) is performed in a solvent selected from the group of polyethylene glycols, polypropylene glycols, glycerol, glyceryl carbonate, C$_1$ to C$_5$-alcohols, 1,2-propanediol, 1,3-propanediol, ethylene glycol, diethylene glycol, 1,2-propylene glycol, 1,3-propylene glycol, 1,2-butanediol, 1,3-butanediol, 2,3-butanediol, 1,4-butanediol, neopentyl glycol, diethylene glycol monomethyl ether, solvents of the formula H—X—Y according to claim 1, dipropylene glycol and a mixture of 2, 3, 4 or 5 of the aforementioned solvents.

3. The process as claimed in claim 1, characterized in that the reaction in process step (b) is performed at a temperature in the range from 40° C. to 120° C. over a period of 0.5 hour to 3 hours.

4. The process as claimed in claim 1, characterized in that the reaction in process step (b) is performed in the presence of one or more compounds selected from NH$_3$, 1,4-diazabicyclo[2.2.2]octane-1,8-diazabicyclo[5.4.O]non-5-ene, triethylamine, triethyldiamine, N-methylimidazole, N,N-dimethylethanolamine, N-methylmorpholine, N-ethylmorpholine, 2,2-dimorpholinodiethyl ether, bis(2-dimethylaminoethyl) ether, N-benzyldimethylamine, N,N'-dimethylcyclohexylamine, M$^2$OH and M$^2$O—R5 where R$^5$ is a hydrocarbyl radical having 1 to 4 carbon atoms and M$^2$ is Li$^+$, Na$^+$, Ca$^{2+}$, or Mg$^{2+}$.

5. The process as claimed in claim 4, characterized in that the reaction in process step (b) is performed in the presence of NH$_3$, NaOCH$_3$, NaOC$_2$H$_5$, KOCH$_3$ or KOC$_2$H$_5$.

6. The process as claimed in claim 5, characterized in that the reaction in process step (b) is performed in the presence of NaOCH$_3$ or NH$_3$.

7. The process as claimed in claim 1, characterized in that the at least one compound of the formula H—X—Y is selected from the group consisting of N-methyl diethanolarnine, N-ethyldiethanolamine and triethanolamine.

8. The process as claimed in claim 1, characterized in that the molar ratio of metal in the compound ML$_4$ in step (a) to the at least one compound from the group consisting of NH$_3$, primary, secondary and tertiary amines, M$^2$OH and M$^2$OR is 1:0.7-1.3.

9. The process as claimed in claim 1, characterized in that the stoichiometric ratio of metal (M) to ligand XY is 1:0.8-1.2.

10. The process as claimed in claim 1, characterized in that M in the formulae (I)-(III) is Sn.

11. The process as claimed in claim 10, characterized in that the compound M(Hal)$_4$ provided in process step (a) is Sn(Cl)$_4$.

12. The process as claimed in claim 10, characterized in that a metal compound of the general formula [(L$^1$)$_{n1}$(L$^2$)$_{n2}$(Cl)$_2$Sn)(IV)] is prepared.

13. A catalyst comprising the metal compounds prepared by the process according to claim 1.

14. A process for the preparation of polyisocyanate polyaddition products comprising the step of adding the catalyst according to claim 13.

15. A process for performance of esterifications and transesterifications comprising the step of adding the catalyst according to claim 13.

16. A process which comprises mixing a silicon resin and the catalyst according to claim 13.

\* \* \* \* \*

UNITED STATES PATENT AND TRADEMARK OFFICE
CERTIFICATE OF CORRECTION

PATENT NO. : 9,079,924 B2  
APPLICATION NO. : 13/504753  
DATED : July 14, 2015  
INVENTOR(S) : Lehmann et al.

Page 1 of 1

It is certified that error appears in the above-identified patent and that said Letters Patent is hereby corrected as shown below:

On the Title Page:

Item (56),

FOREIGN PATENT DOCUMENTS

"DE 242617 A1 2/1987"

should read "DD 242 617 A1 2/1987"

Item (56),

OTHER PUBLICATIONS

"Tzsahach, A."

Should read "Tzschach, A"

Signed and Sealed this  
Twenty-second Day of March, 2016

Michelle K. Lee  
*Director of the United States Patent and Trademark Office*